United States Patent
Andreyev et al.

(10) Patent No.: US 11,806,182 B2
(45) Date of Patent: Nov. 7, 2023

(54) METHOD AND APPARATUS FOR AMYLOID SCREENING

(71) Applicant: KONINKLIJKE PHILIPS N.V., Eindhoven (NL)

(72) Inventors: Andriy Andreyev, Willoughby Hills, OH (US); Douglas B. McKnight, Chardon, OH (US); Nathan Serafino, Lyndhurst, OH (US); Dane Pittock, Lyndhurst, OH (US); Chuanyong Bai, Solon, OH (US); Chi-Hua Tung, Aurora, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/270,224

(22) PCT Filed: Aug. 13, 2019

(86) PCT No.: PCT/EP2019/071702
§ 371 (c)(1),
(2) Date: Feb. 22, 2021

(87) PCT Pub. No.: WO2020/038773
PCT Pub. Date: Feb. 27, 2020

(65) Prior Publication Data
US 2021/0298701 A1    Sep. 30, 2021

Related U.S. Application Data

(60) Provisional application No. 62/720,151, filed on Aug. 21, 2018.

(51) Int. Cl.
*A61B 6/00* (2006.01)
*G16H 50/30* (2018.01)
*A61B 6/04* (2006.01)

(52) U.S. Cl.
CPC .............. *A61B 6/501* (2013.01); *A61B 6/04* (2013.01); *A61B 6/4057* (2013.01);
(Continued)

(58) Field of Classification Search
CPC ........... A61B 6/00; A61B 6/501; G16H 50/30
See application file for complete search history.

(56) References Cited

U.S. PATENT DOCUMENTS 6,808,308 B2    10/2004  Scanwell
11,484,278 B2 *  11/2022  Verma ................ A61B 5/02755
(Continued)

FOREIGN PATENT DOCUMENTS

JP      2010197140 A     9/2010
JP      2015222193 A    12/2015
(Continued)

OTHER PUBLICATIONS

International Search Report and Written Opinion of PCT/EP2019/071702, dated Nov. 4, 2019.

*Primary Examiner* — Angela M Hoffa
*Assistant Examiner* — Younhee Choi (57) ABSTRACT

A device (10) for performing an amyloid assessment includes a radiation detector assembly (12) including at least one radiation detector (14). At least one electronic processor (20) is programmed to: detect radiation counts over a data acquisition time interval using the radiation detector assembly; compute at least one current count metric from the detected radiation counts; store the at least one current count metric associated with a current test date in a non-transitory storage medium (26); and determine an amyloid metric based on a comparison of the at least one current count metric with a count metric stored in the non-transitory storage medium associated with an earlier test date.

15 Claims, 6 Drawing Sheets

(52) U.S. Cl.
CPC .......... *A61B 6/4258* (2013.01); *A61B 6/5217* (2013.01); *G16H 50/30* (2018.01)

(56) References Cited

U.S. PATENT DOCUMENTS

| | | |
|---|---|---|
| 2003/0111609 A1 | 6/2003 | Zeng |
| 2004/0253647 A1 | 12/2004 | Jiang |
| 2008/0021256 A1 | 1/2008 | Srinivas |
| 2010/0001192 A1 | 1/2010 | Ange |
| 2010/0145194 A1 | 6/2010 | Joshi |
| 2010/0331676 A1 | 12/2010 | Carpenter |
| 2013/0084245 A1 | 4/2013 | Blavk |
| 2013/0259801 A1 | 10/2013 | Chenou |
| 2014/0086836 A1 | 3/2014 | Burnham |
| 2014/0319360 A1* | 10/2014 | Wieczorek ............. A61B 6/469 250/363.04 |
| 2019/0320989 A1* | 10/2019 | Verma ....................... G01T 1/16 |

FOREIGN PATENT DOCUMENTS

| | | |
|---|---|---|
| WO | 199514234 A1 | 11/1993 |
| WO | 2017048904 A1 | 3/2017 |

\* cited by examiner

METHOD AND APPARATUS FOR AMYLOID SCREENING

CROSS-REFERENCE TO PRIOR APPLICATIONS

This application is the U.S. National Phase application under 35 U.S.C. § 371 of International Application No. PCT/EP2019/071702, filed on Aug. 13, 2019, which claims the benefit of U.S. Provisional Patent Application No. 62/720,151, filed on Aug. 21, 2018. These applications are hereby incorporated by reference herein.

FIELD

The following relates generally to the image acquisition arts, brain image arts, beta amyloid imaging arts, and related arts.

BACKGROUND

An elevated beta-amyloid deposition in human brain has been linked to eventual Alzheimer diagnosis. Timely detection of amyloid deposits could provide a necessary preventive procedures aimed at better control of this devastating condition. Recently, new positron emission tomography (PET) radiotracers have been developed to detect increased deposition of amyloid plaque. Other types of chronic neurological diseases have also been correlated with build-up of characteristic amyloids, such as Parkinson's disease which has been correlated with build-up of the amyloid alpha-synuclein, and protein deposits of other types have been correlated with other neurological diseases, such as tau protein build-up which has been correlated with Chronic Traumatic Encephalopathy (CTE).

While being effective in diagnosis of amyloid plaque, conventional PET/computed tomography (CT) systems cannot be routinely prescribed to the general population to monitor and detect the disease in its early stage. This even includes those individuals with known high-risk factors such as genetic predisposition to an Alzheimer diagnosis. The major obstacles are cost which can be on the order of several thousand dollars (see, e.g., https://www.alzforum.org/news/community-news/100m-ideas-cms-blesses-study-evaluate-amyloid-scans-clinical-practice) and relatively high radiation dose, linked to such PET/CT scan (on the order of at least 5 mSv).

The following discloses new and improved systems and methods to overcome these problems.

SUMMARY

In one disclosed aspect, a device for performing an amyloid assessment includes a radiation detector assembly including at least one radiation detector. At least one electronic processor is programmed to: detect radiation counts over a data acquisition time interval using the radiation detector assembly; compute at least one current count metric from the detected radiation counts; store the at least one current count metric associated with a current test date in a non-transitory storage medium; and determine an amyloid metric based on a comparison of the at least one current count metric with a count metric stored in the non-transitory storage medium associated with an earlier test date.

In another disclosed aspect, a radiation detector assembly include a back radiation detector and two side radiation detectors. The back radiation detector and the two side radiation detectors are arranged to define a cavity sized to receive a head with the back radiation detector arranged to view a backside of the head disposed in the cavity and the two side radiation detectors arranged to view left and right sides of the head disposed in the cavity.

In another disclosed aspect, a method for performing a clinical assessment includes: obtaining imaging data using a radiation detector assembly including at least one radiation detector mounted in or on a patient support on which the patient is positioned to view a head of the positioned patient; detecting radiation counts from a radiotracer administered to the patient that binds with a targeted protein over a data acquisition time interval; computing at least one current count metric from the detected radiation counts; and determining a metric of deposits of the targeted protein in the head of the positioned patient based on a comparison of the at least one current count metric with a previous count metric.

One advantage resides in providing a low cost device for assessing build-up of beta amyloid or another amyloid or other targeted protein in the brain.

Another advantage resides in providing an imaging device in which a patient to be imaged takes a reduced radiopharmaceutical dose.

Another advantage resides in providing a device for early detection of gradual build-up of amyloid deposits.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Beta amyloid (Aβ) deposits in brain tissue have been correlated with certain neurodegenerative diseases such as Alzheimer's disease. Other types of amyloid deposits have been correlated with other neurological diseases, such as alpha-synuclein which has been correlated with Parkinson's disease, and even more generally various types of protein deposits have been correlated with various neurological diseases, e.g. tau protein deposits have been correlated with Chronic Traumatic Encephalopathy (CTE). PET or single photon emission computed tomography (SPECT) imaging can be used in conjunction with a radiotracer that preferentially binds to Aβ in order to image beta amyloid deposits in the brain, thus providing a screening tool for detecting and monitoring these diseases. However, PET or SPECT is not an ideal choice for patient screening. The techniques are expensive to perform, and require delivery of a relatively high radioactive dose to the patient.

It is recognized herein that some of these disadvantages of PET or SPECT can be alleviated by eliminating the imaging aspect, or to a lesser extent by employing imaging of lower resolution and/or reduced dimensionality (e.g. acquiring a 2D or 1D map). To perform imaging, it is necessary to have sufficient radiotracer administered so that the concentration of radiotracer in each voxel of the image (or at least in those voxels with substantial amount of the targeted protein) is at a detectable level. By contrast, if another metric of the deposits of the targeted protein in the head of the patient is used, such as total counts from the entire head, then the minimum requisite dosage of radiotracer can be substantially reduced (e.g., by an order of magnitude or more in some embodiments).

However, by such an approach the sensitivity becomes less, as the amount of information is reduced by loss of the spatial resolution provided by imaging and as the signal-to-noise ratio is reduced by a reduced radiotracer dosage. In some embodiments disclosed herein, the metric of deposits of the targeted protein in the head is based on a comparison of a current count metric with a previous count metric (e.g., obtained in an earlier test date). This automatically normalizes out individual factors and focuses the metric on change over time, which is more likely to be clinically significant as compared with a metric that is referenced to nominally similar measurements in a nominally similar patient cohort.

In embodiments disclosed herein, lower-cost instrumentation is employed, and reduced radiotracer dosage is administered to the patient. In some embodiments, a low cost radiation detector is integrated into the head region of a patient couch, along with a radiation shielding collar arranged to fit around the patient's neck to reduce detection of stray radiation from the torso region. The goal is to measure the total counts for a fixed acquisition time (or equivalently, the count rate) measured after delivery of a radiotracer targeting the amyloid or other targeted protein deposits. Further cost reduction is achieved in some embodiments by detecting singles rather than coincidences, and/or omitting or simplifying image generation, and/or omitting the conventional coincidence detection circuitry and/or radiation collimator (with consequent loss of imaging capability). Low dose is achieved in part by measuring counts for a large portion of the brain, or for the entire brain; rather than using a local radiation probe or effectively partitioning the detected counts into image voxel values by way of image reconstruction.

In other embodiments, multiple radiation detectors are arranged surrounding a portion or all of the head, thereby further maximizing detected counts and allowing for further reduction in radiotracer dosage. Various implementations can be implemented, such as a three- or four-detector slab design with a backside slab embedded in the table, two side slabs arranged left and right of the head, and an optional crown slab positioned "above" the crown of the head. The side and crown slabs can be mounted on rails and slid into contact with the sides and crown of the head, thereby also providing stabilization of the head and motion suppression. A radiation-shielding collar fitted around the patient's neck may provide further head stabilization and also operate to block stray counts from radiotracer concentrations in the torso or other body portions "below" the head. A further detector slab could be placed in front of the patient's face, but the potential for inducing claustrophobia may be a factor in deciding whether to include (or use) this additional detector slab.

It is noted that, as used herein, the term "patient" broadly denotes the person undergoing the clinical assessment of beta amyloid (or other targeted protein) deposits in the brain (i.e. head). The patient may be a patient diagnosed with early-onset Alzheimer's disease or another chronic neurological condition whose clinical progression is being monitored, or the patient may be a healthy individual who is merely undergoing screening for beta amyloid deposits. Indeed, an advantage of the disclosed approaches is that their low cost and reduced radiotracer dosage makes these approaches well-suited for use in screening healthy patients, possibly on an out-patient basis or during a routine medical examination (e.g. during the patient's annual physical examination).

It is recognized herein that providing a fair comparison for the screening is a difficult challenge. In the illustrative examples, no external baseline (for example, derived from similar measurement of a cohort of similar patients, or from measurements taken from a "normal" portion of the patient's body) is relied upon; rather, the test is designed to be performed on a given patient at successive test dates, in order to detect a rise over time in the counts that may be indicative of an increase in $A\beta$ deposits in that patient's brain.

Further aspects disclosed herein relate to data quantification, for which various metrics can be used alone or in combination. Counts at a fixed time after administration of the radiopharmaceutical (i.e. radiotracer) can be a suitable metric, but this relies upon precise timing of the measurement and might be susceptible to differences in radiotracer dosage and uptake between sessions due to metabolic differences or so forth. Another approach is to measure the counts-versus-time curve, from which various metrics such as peak counts, FWHM of the uptake curve, ramp-up slope, washout decay constant, area-under-curve, or so forth may be extracted. Here the desire for high temporal resolution in the counts-versus-time curve may be balanced against the need for sufficient counts statistics in each time bin. In any case, the metrics may be adjusted or normalized for injected quantity of the radiotracer, patient weight or body mass index (BMI), age (to account for natural buildup of $A\beta$ due to aging), and/or other variables such as gender or ethnicity.

In some embodiments disclosed herein, no imaging is performed. This permits cost savings such as elimination of timestamping circuitry and coincidence detection and/or the use of radiation collimators (e.g. honeycomb collimators mounted on the front of the radiation detectors), use of a radiation detector with coarse resolution or even a single large area detector (also facilitated by use of low radiotracer dose and consequent reduction in potential for pileup of counts), elimination of scatter correction, and enabling use of a stationary detector that does not completely encircle the head of the patient. It is further recognized that the energy window for singles detection can be enlarged toward the low-energy end to intentionally count in-elastically scattered events, again enabling further dose reduction. Scattered events are problematic for imaging since the sourcing radioactive decay event does not generally lie on the "line of response" defined by a coincidence or a radiation collimator, and scatter events are largely removed by employing an energy window that filters out scattered detections that have lost energy during the (inelastic) scattering. However, if imaging is not performed, as in some protein deposit assessment approaches disclosed herein, then these scattered events can be retained by extending the energy window on the low energy side, thereby increasing the total counts. By such strategies, it is estimated that dose reduction of as much as a factor of 1000 compared with conventional PET may be achievable, making the Aβ screening dose comparable to a routine dental x-ray.

In other embodiments disclosed herein, imaging is performed. In this case, radiation detectors providing multiple viewpoints are provided, such as the mentioned design with a backside detector, side detectors, and an optional crown detector. A low resolution image is sufficient to provide some visual context for the clinician, since the clinical results are derived from the total or average counts. In a PET embodiment coincidence detection is employed for spatial encoding of the counts. In a SPECT embodiment, a radiation collimator (e.g., a honeycomb collimator) provides the spatial encoding of the counts. Advantageously, since the radiation detectors are stationary (except perhaps for a pre-acquisition positioning of the detector slabs against the patient's head) the collimator can be provided as a set of slats or a grid that is inserted into a receiving slot of the radiation detector or its mount when imaging is desired. In one embodiment, the "imaging" is a one-dimensional (1D) counts profile line. As it has been observed that the Aβ deposits tend to accumulate in the outer regions of the brain, the resulting profile line is expected to exhibit peaks at the outer regions and a dip in the center, and this shape and possibly an extracted quantification such as the peak-to-valley ratio can be leveraged for providing the clinician with a visual representation, and optionally also for quantitative data.

Figure 1:
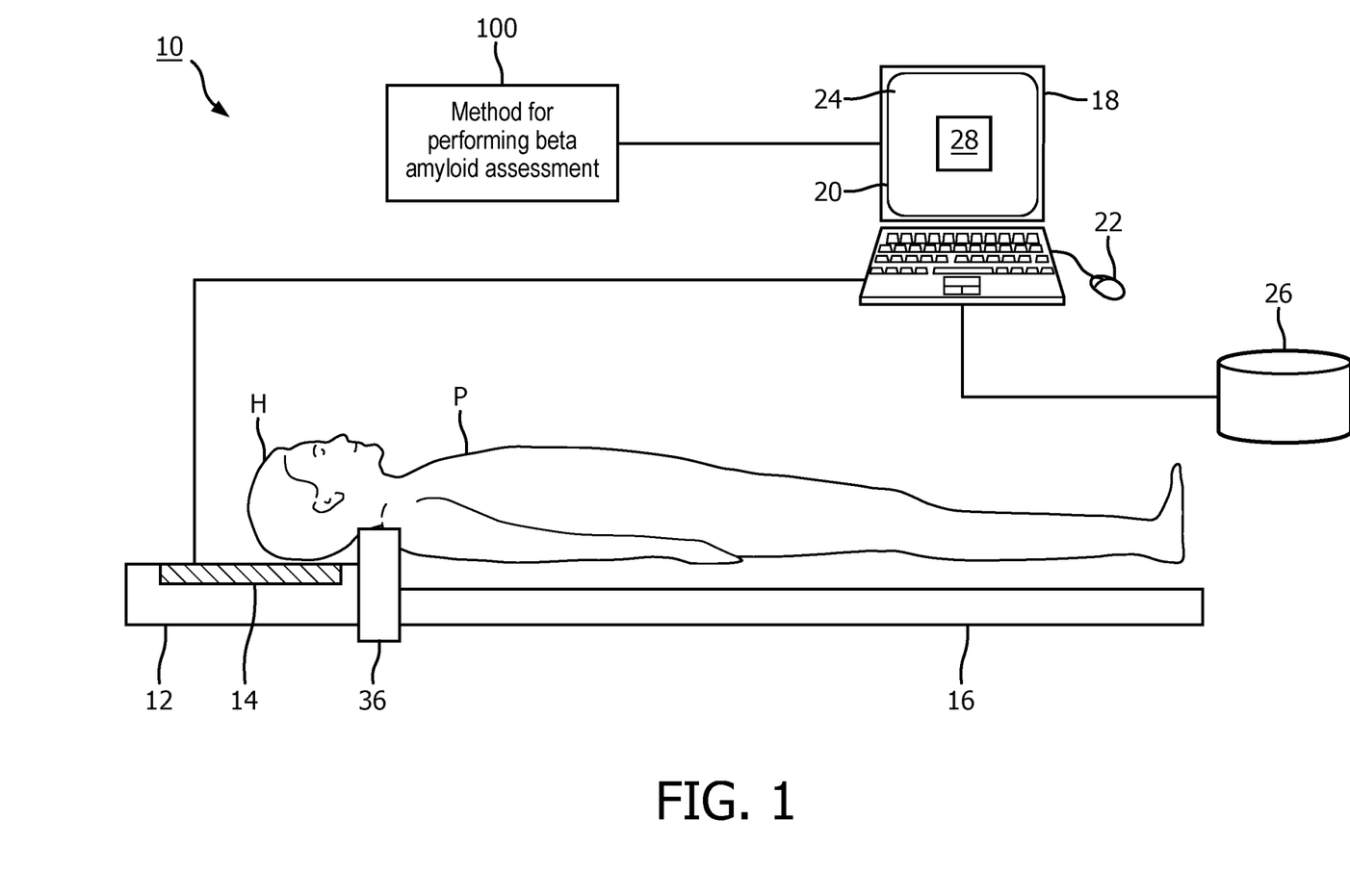
FIG. 1 diagrammatically shows a device for performing beta amyloid assessment according to one aspect.

With reference to FIG. 1, an illustrative device or system 10 for performing beta amyloid assessment is shown. (In the following, beta amyloid assessment is described, which is useful for assessing a patient for a correlated chronic neurological disease such as Alzheimer's disease. In other embodiments, deposits of a different targeted amyloid or more generally different targeted protein may be assessed; this is done by choosing a radiotracer for administration to the patient that preferentially binds to the particular targeted amyloid or more generally to the particular targeted protein). As shown in FIG. 1, the system 10 includes a radiation detector assembly 12 with at least one radiation detector 14. In the illustrative example of FIG. 1, the radiation detector assembly 12 consists of a single radiation detector slab 14 that is embedded in the head region of a patient support 16; in other embodiments described herein the radiation detector assembly may include two or more detector slabs, e.g. additional slabs arranged left and right of the head, and further optionally at the crown of the head. It is also noted that each such detector slab may be constructed as two or more operationally independent detector tiles, e.g. a 2×2 array of detector tiles may make up the single radiation detector slab shown in FIG. 1. The radiation detector assembly 12 can be integrated with, or otherwise attached to, the patient support 16 on which a patient P lies. The radiation detector assembly 12 is sized and configured to receive a portion (i.e., head H) of a patient as the patient lies on the patient support 16.

The device 10 may also include, or be otherwise connected with a workstation 18 comprising a computer or other electronic data processing device with typical components, such as at least one electronic processor 20, at least one user input device (e.g., a mouse, a keyboard, a trackball, and/or the like) 22, and a display device 24. It should be noted that these components can be variously distributed. For example, the electronic processor 20 may include a local processor of a workstation terminal and the processor of a server computer that is accessed by the workstation terminal. In some embodiments, the display device 24 can be a separate component from the computer 18. The workstation 18 can also include one or more databases or non-transitory storage media 26. The various non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth. They may also be variously combined, e.g. a single server RAID storage. The display device 24 is configured to display a graphical user interface (GUI) 28 including one or more fields to receive a user input from the user input device 22.

In particular, the workstation 18 is operatively connected with the radiation detector assembly 12 in order to receive counts of radiation detection events from the at least one radiation detector 14. These counts may be variously processed by the workstation 18 and/or preprocessed by electronics of the radiation detector assembly 12 (such electronics not shown in FIG. 1) to perform various filtering or the like of the acquired counts data. For example, energy filtering can be applied to filter out counts whose energy lies outside of a defined energy window that is positioned to encompass the energy or energy range of radio-emission particles emitted by the radiotracer. For example, a positron-emitting PET radiotracer emits oppositely directed 511 keV gamma rays emanating from each positron-electron annihilation event; hence, in this case the energy window suitably encompasses 511 keV. As previously noted, for non-imaging embodiments it is contemplated to design the energy window to extend to substantially lower energy to capture in-elastically scattered gamma rays that have lost energy due to the scattering and hence are detected at a particle energy below 511 keV. Some radiotracers emit gamma rays, beta particles, alpha particles, and/or other radio-emissions over a range of energies, in which case the energy window preferably extends over this range. It is also contemplated for the energy window to be a configurable parameter in order to be tuned for a particular type of radiotracer being used for a particular patient assessment, thereby increasing flexibility of the device.

Figure 2A:
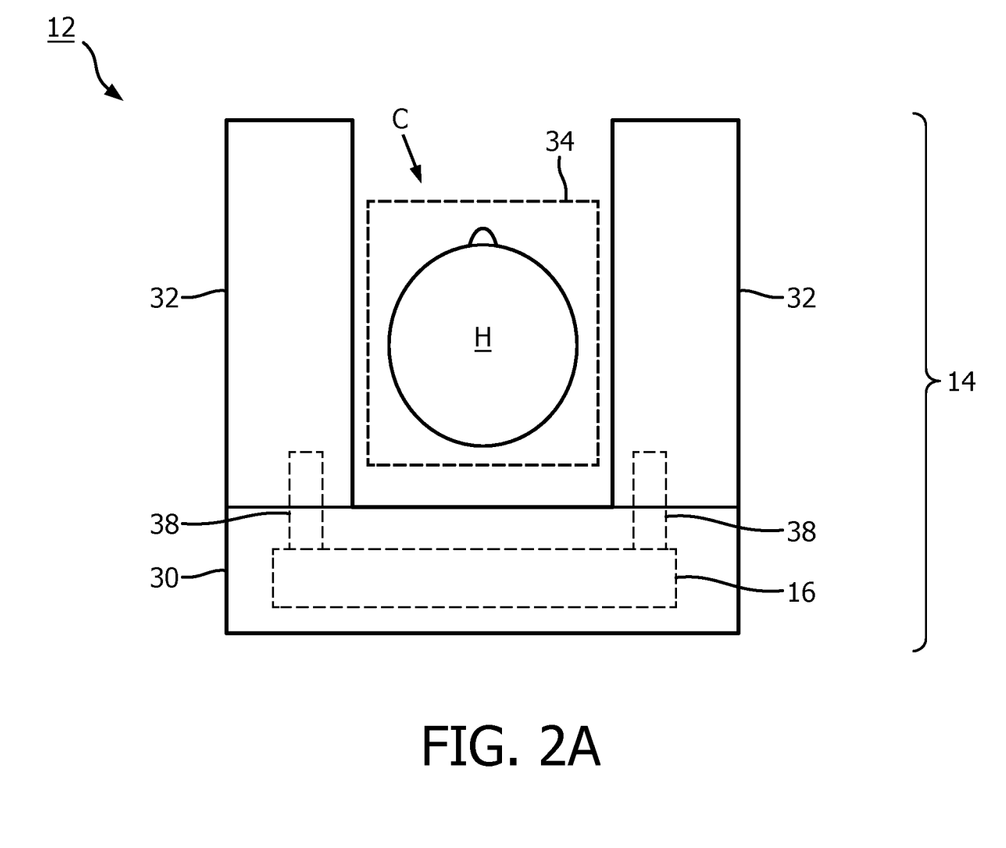
FIGS. 2A-2C diagrammatically show a radiation detector assembly of the device of FIG. 1.
Figure 2B:
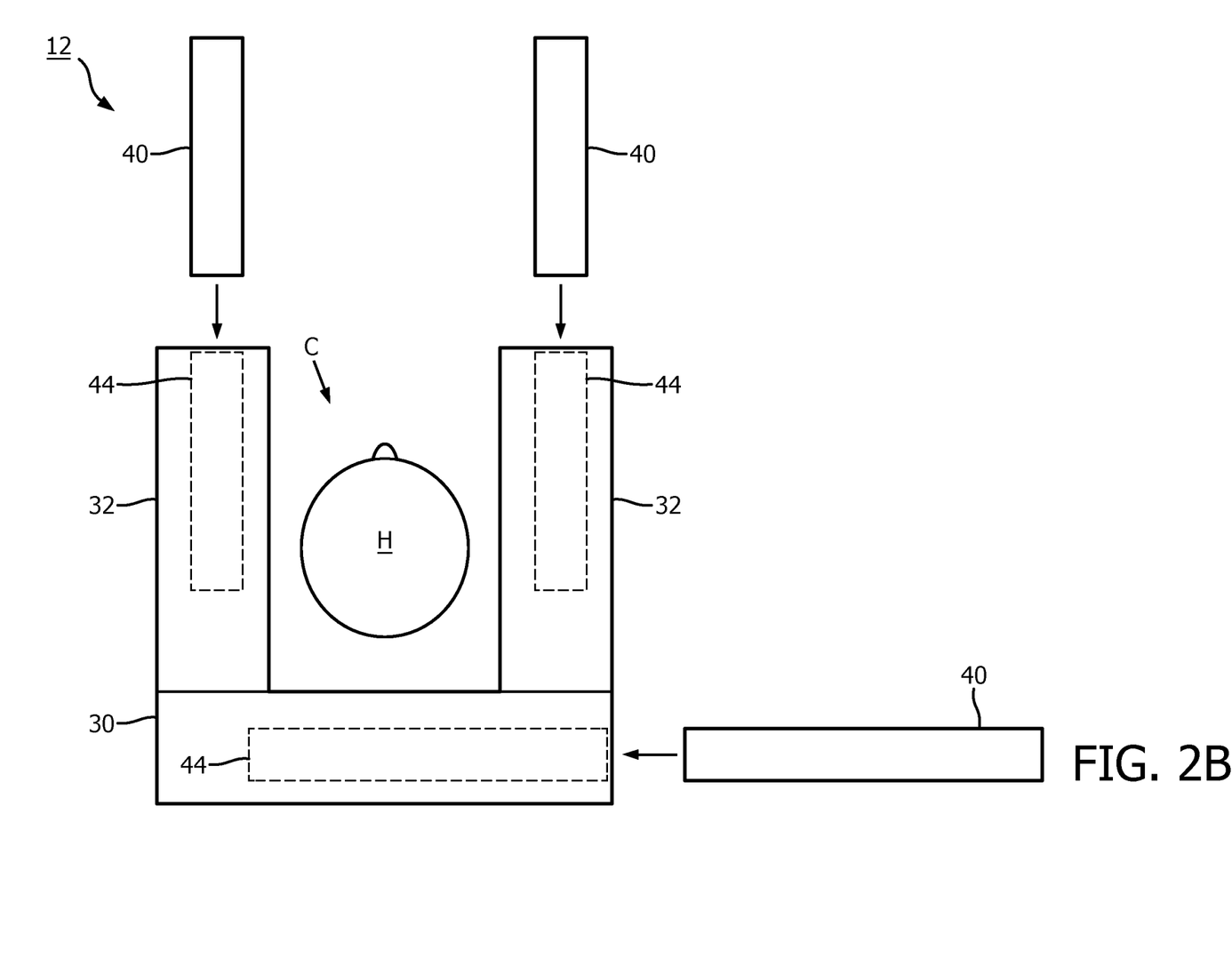
Figure 2C:
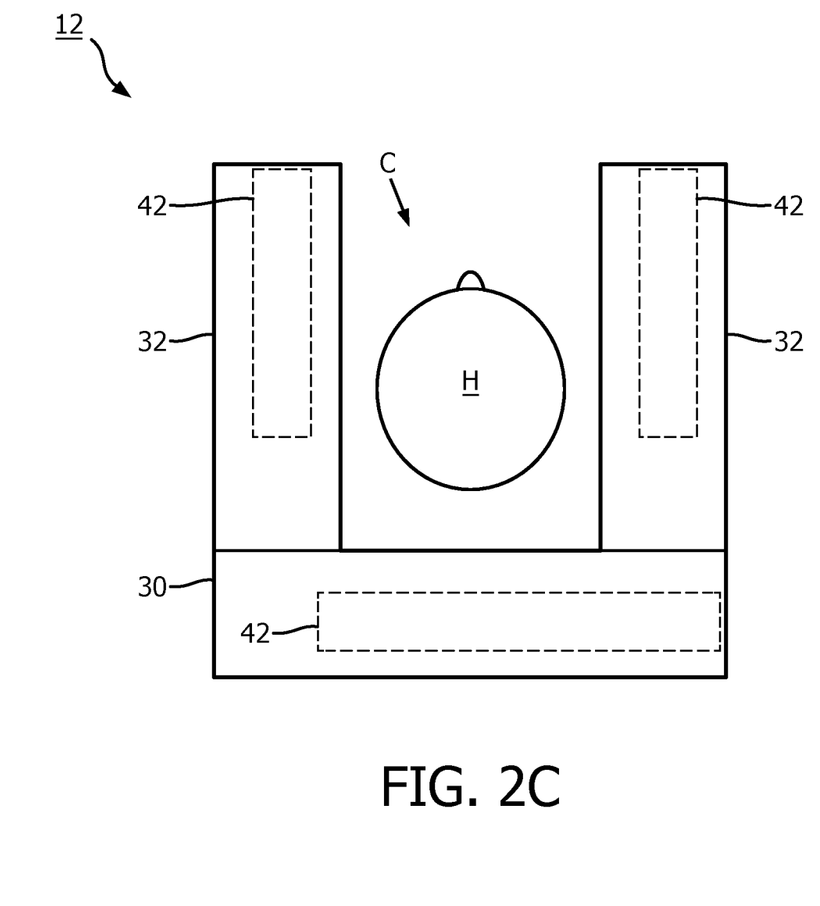

FIGS. 2A-2C show another example embodiment of the radiation detector assembly 12. FIG. 2A shows a "back" view of the radiation detector assembly. As shown in FIG. 2A, the radiation detector assembly 12 includes several radiation detectors 14, such as a back radiation detector 30 (e.g., positioned the same as the single radiation detector 14 depicted in FIG. 1) and two side radiation detectors 32. The back radiation detector 30 and the two side radiation detectors 32 are arranged or otherwise configured to define a cavity C sized to receive the head H of the patient. The back radiation detector 30 is arranged to view a backside of the head disposed in the cavity C, and the two side radiation detectors 32 are arranged to view left and right sides of the head disposed in the cavity. In one example, the back radiation detector 30 and the two side radiation detectors 32 each have a planar radiation detecting surface (as illustrated). In another example, the back radiation detector 30 and the two side radiation detectors 32 have curved radiation detecting surfaces (not shown) which are shaped to conform with a shape of the head disposed in the cavity C. The side detectors 32, if provided, yield additional counts to enable further reduction in the administered radiopharmaceutical dosage. In some embodiments, a crown radiation detector 34 (shown by dashed lines) is included to further define the cavity C and to provide still further counts, and arranged to view a crown (i.e. top) of the head H disposed in the cavity.

In some embodiments, the radiation detector assembly 12 further includes a radiation shielding collar 36 (see FIG. 1) comprising a radiation-absorbing material (e.g. a high atomic weight material such as lead or a composite or other matrix containing a high atomic weight element such as leaded glass) and shaped and sized to be disposed around a portion (i.e., neck) of the patient. The optional radiation shielding collar 36 blocks stray radiation from the torso and/or other portions of the body from reaching the detector(s) 14 surrounding the head H, and also may serve to mechanically stabilize the head H.

In some embodiments, the radiation detector assembly 12 does not include robotic actuators configured for moving the radiation detectors 14 during a data acquisition time interval over which radiation counts are detected using the radiation detector assembly. In other embodiments, adjustable supports 38 are attached to the side radiation detectors 32 and the patient support 14 to move and position the side radiation detectors at an adjustable distance from the cavity C.

As shown in FIG. 2A, the radiation detector assembly 12 does not include a radiation collimator, nor does the device 10 include timestamping circuitry for assigning timestamps to radiation counts detected using the radiation detector assembly. (Note, however, that in contrast to timestamping individual counts, a test date may be assigned for an acquired data set of counts). In other embodiments, either at least one radiation collimator plate 40 (see FIG. 2B) or coincidence detection circuitry 42 (see FIG. 2C) is included with the radiation detector assembly 12 collimate radiation detected by the radiation detectors 14. (More specifically, the collimator plate 40 passes to the coupled radiation detector only radiation travelling along a line or narrow-angle cone, so that the detected radiation is collimated). Each of the back radiation detector 30 and the two side radiation detectors 32 has collimator mounting hardware 44 via which one of the radiation collimator plates is mountable to the planar radiation detecting surface. In some examples, the radiation collimator plate 40 can include a slat or honeycomb radiation collimator plate, and the collimator mounting hardware 44 comprises a corresponding slit configured to receive and hold the slat or honeycomb collimator plate. With such collimation, the at least one electronic processor 20 can be programmed to reconstruct the detected radiation counts into an image (e.g., a one-dimensional image in the case of a slat collimator, or a two- or three-dimensional image in the case of a honeycomb collimator). Such image reconstruction can employ any suitable image reconstruction technique such as one conventionally employed in reconstructing SPECT imaging data. In another embodiment, if the radiotracer is a PET radiotracer that emits positrons that decay into oppositely directed 511 keV gamma rays, then coincidence detection can be employed in which coincident 511 keV detection events are detected using a suitable time window and each pair of 511 keV detections form a count. In this case, any conventional PET reconstruction technique can be employed to reconstruct the counts into an image. In some examples, the radiation detector assembly 12 is configured to detect radiation counts emanating from at least one half of tissue of a brain monitored by the radiation detector assembly.

With returning reference to FIG. 1, the system 10 is configured to perform a method or process 100 for performing a beta amyloid (or other targeted amyloid or protein) assessment. To this end, the non-transitory storage medium 26 stores instructions which are readable and executable by the at least one electronic processor 20 of the workstation 18 to perform disclosed operations including performing the method or process 100 for performing a beta amyloid assessment. In some examples, the method 100 may be performed at least in part by cloud processing.

Figure 3:
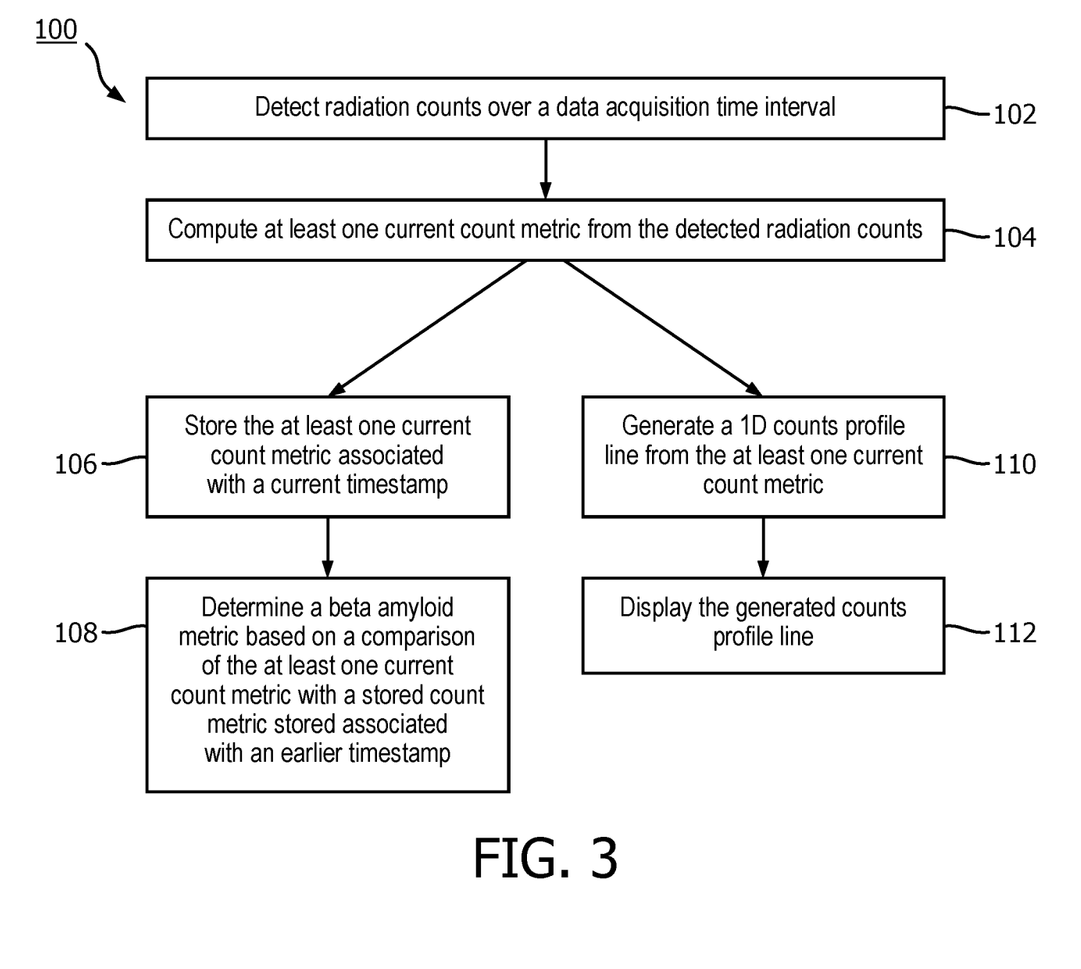
FIG. 3 shows an exemplary flow chart operation of the device of FIG. 1.

With reference to FIG. 3, an illustrative embodiment of the method 100 for performing a beta amyloid assessment is diagrammatically shown as a flowchart. To begin the method 100, a patient is positioned (e.g., laid) on the patient support 16. A radiotracer is then administered to the patient while positioned on the patient support 16. (Alternatively, the radiotracer may be administered prior to placement of the patient on the patient support; however, administering the radiotracer with the patient already positioned on the patient support can provide for more precise timing between the administration and the time interval for counts measurement). At 102, the at least one electronic processor 20 is programmed to control (or merely read, in some embodiments) the detectors 14 of the radiation detector assembly 12 to detect radiation counts over a data acquisition time interval. The detecting includes continuously detecting singles radiation counts from at least one-half of the brain (in some preferred embodiments, although monitoring a smaller portion of the brain is also contemplated) of the positioned patient over the data acquisition time interval. In some examples, the singles radiation counts are detected without collimation of the radiation, and without determining and assigning timestamps to individual counts.

At 104, the at least one electronic processor 20 is programmed to compute at least one current count metric from the detected radiation counts. In some examples, the at least one current count metric includes at least one of a count rate and a total counts detected over the data acquisition time interval. In this example, the computing of the at least one current count metric includes scaling the at least one current count metric by one or more of patient weight, patient age, patient gender, and patient ethnicity. The scaling may be empirically determined, e.g. using a look-up table that applies a scaling factor on the basis of patient age, or a scaling factor proportional to patient weight, or so forth. As another contemplated adjustment, the radioactivity of the radiotracer may be measured prior to administration to the patient or during administration (e.g. using a Geiger counter monitoring radioactivity of a fluid tube intravenously feeding radiotracer solution into a blood vessel of the patient). The count metric may be scaled proportional to the actually measured radioactivity of the radiotracer. This adjustment accounts for day-to-day variability in the injected dose of the radiotracer.

At 106, the at least one electronic processor 20 is programmed to store the at least one current count metric associated with a current test date in the non-transitory storage medium 26. (The test date is associated with the data set as a whole, as opposed to timestamps of individual radiation detection counts. As such it may optionally be of relatively low temporal resolution, e.g. storing the calendar date but not a time-of-day).

At 108, the at least one electronic processor 20 is programmed to determine a beta amyloid metric based on a comparison of the at least one current count metric with a count metric stored in the non-transitory storage medium 26 associated with an earlier test date. The beta amyloid metric (or, more generally, the amyloid metric, or even more generally the metric of deposits of the targeted protein in the head H of the patient P) may, for example, be a percent change between the current count metric and the count metric of the earlier test date.

At 110, in the case of certain imaging embodiments, the at least one electronic processor 20 is programmed to generate a one-dimensional (1D) counts profile line from the measured total number of counts or the count rate, based on an image reconstructed from spatial localization of the events provided by a collimator in SPECT-type imaging, or by PET-type coincidence detection).

At 112, the at least one electronic processor 20 is programmed to control the display 24 to display the beta amyloid metric and (if generated) the generated counts profile line having peaks at outer regions thereof and a trough at a center portion thereof. Other information may be displayed such as the current counts metric and the counts metric of the earlier test date. If there are two or more past tests stored in the non-transitory storage medium 26, then optionally one or more trend lines can be plotted, such as plotting the counts metric for each test as a function of test date. Display of such a trend line allows for the clinician to immediately visually perceive whether the counts metric (and, by inference, the beta amyloid deposits) have been increasing, and if so at what rate. These various metrics may also have associated uncertainties or statistical significance values, based on empirical analyses of how large the test-over-test count metric should be before it is given clinical significance. It is also noted that the beta amyloid metric and any other displayed metrics (e.g. the trend line of count metrics over several tests) is merely clinical information for consideration, in conjunction with other information such as physical examination, inquiry into patient-reported symptoms such as level of mental recall, or so forth, by the clinician in assessing whether the patient P should be diagnosed as having Alzheimer's disease (or other disease associated with build-up of the targeted amyloid or protein in the brain).

The beta amyloid metric (generated at 108) and/or the counts profile line (generated at 110) may be additionally or alternatively used in follow-up treatment of the patient. For example, if a medication is administered to suppress amyloid deposits, the patient may monitored during the medication treatment (e.g., using the beta amyloid assessment method 100) to determine the effectiveness of the medication regimen. Advantageously, the low radiopharmaceutical dosage and use of the system 10 (instead of using a full PET imaging system with its accompanying high cost and requisite higher radiopharmaceutical dosage) allow for more frequent monitoring of the patient.

While the illustrative examples employ the dedicated system 10, it is noted that the beta amyloid metric and the counts profile line obtained by the system 10 can in alternative embodiment be acquired using a conventional PET imaging system, for example including coincidence detection circuitry and configured to perform image reconstruction.

Figure 4:
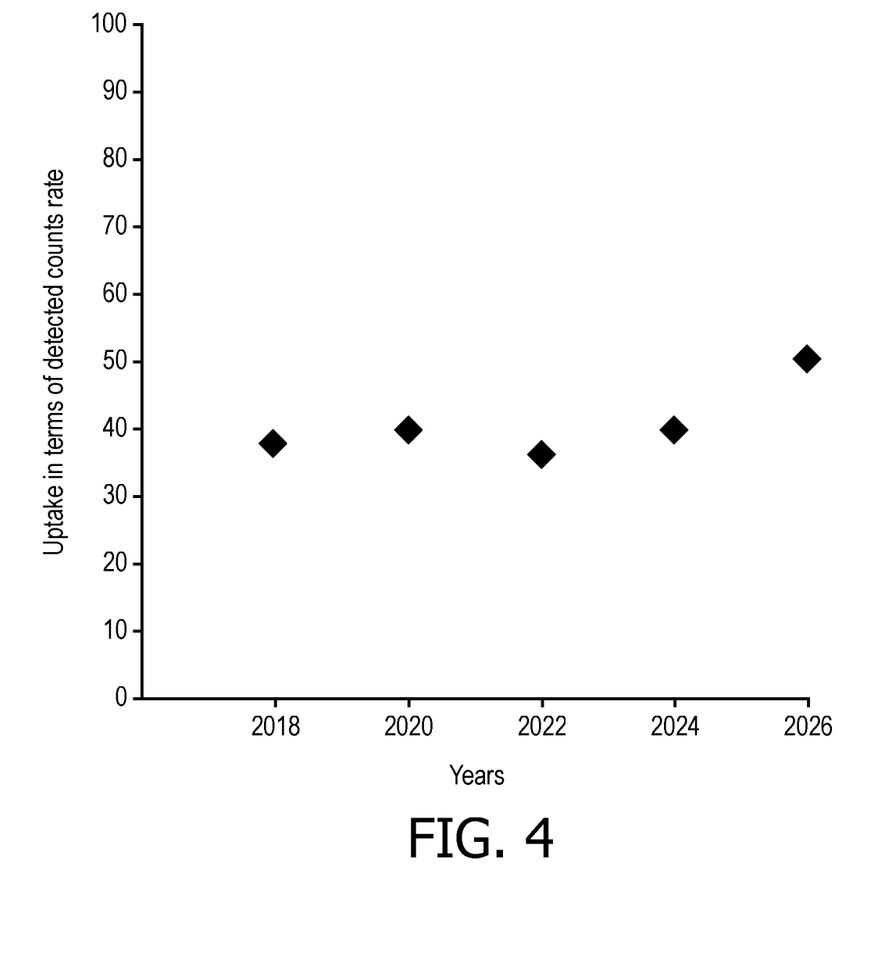
FIG. 4 shows a counts profile line graph from data collected by the device of FIG. 1.

FIG. 4 shows a hypothetical example of a generated counts profile (i.e. trend) line. As diagrammatically shown in FIG. 4, an uptake (measured, for example, by a counts metric such as count rate or total counts) of an amyloid tracer can be compared over the time for successive test dates (e.g., tests may be performed every two years, e.g. in years 2018, 2020, 2022, 2024, and 2026 in the hypothetical example of FIG. 4). If a current test indicates a statistically significant increase in uptake (such as the test in year 2026 in hypothetical FIG. 4, which shows a relatively large increase over the result in year 2024 and preceding years), the patient may be referred to further tests, especially if he is in the risk group based on age, occupation or family history. Another test may be performed using the apparatus of FIG. 1 after some period of time to confirm the trend. At least two repeated scans (e.g., with some gap in time) may be considered clinically significant so as to contribute (with other factors such as patient-reported mental acuity) to an amyloidosis risk assessment.

It may be noted that the foregoing approach assumes that there are one or more past tests yielding past count metric(s) against which the count metric of the current test is compared. The first time the test is run on a given patient, there will be no past results to compare against and so it will be difficult or impossible to draw clinically useful information from that first test in isolation. In some embodiments, it is contemplated to compare the first test result against a typical value for a cohort of similar patients—if the current patient has much higher count rate (or other count metric) compared with these similar patients then some conclusion might be drawn by the clinician, especially if it is supported by patient-reported forgetfulness or other indications of onset of Alzheimer's disease. However, as emphasized herein it is expected that clinical conclusions drawn from a trend of test results over several years is more likely to yield clinically meaningful information.

Example

The device 10 is configured to provide a low cost amyloid screening tool which makes large scale (e.g., population level) screening for the risk of amyloid accumulation available. The patient is injected with microdoses of amyloid specific radiotracer and, after the uptake time, the amount of radioactivity increase in patient head is assessed using, for example, a gamma camera to count the number of acquired single hits. The scan is repeated on an annual or clinician-prescribed basis, and the obtained singles count rates (and/or other count metric) for the current test are compared with the count rates for past tests to determine the trend for potential amyloid plaque accumulation. If the trend becomes positive (uptake increase in more recent tests), then the patient may be referred for further tests. Such proposed screening is affordable as inexpensive detectors can be used to measure the single rates, as well as only microcuries of the radioactivity may be used, as there is no need to create tomographic images.

The device 10 is configured to increase affordability and reduce a radiation burden for the patient to make the amyloid screening as available as possible, comparable to other routine examinations such as dental and chest X-ray (0.1-0.005 mSv), and much lower than even that for low-dose CT lung screening (1.5 mSv).

It is contemplated that with such a device, patients who belong to a group at elevated risk for onset of Alzheimer's disease, or even belonging to the general population, would undergo examination annually (or on other clinically established rate) using the device 10. A patient exam starts from injection of a small controlled amount of radioactive tracer that binds to amyloid plaque, e.g. florbetapir or flutemetamol. After an uptake period, the patient's head is being scanned on a nuclear medicine camera working in singles detection mode without collimation. Only the singles rate (or total number of singles needs to be recorded).

The detectors 14 may optionally wrap around the patient's head with additional radiation sensitive blocks, as described for example with reference to FIGS. 2A-2C. Scanning in sitting or standing position is also contemplated. It is also advantageous to shield the detector part from the radioactivity coming from the rest of the body as much as possible, for example using the illustrative radiation shielding collar 36, and/or by placing a lead shirt over the patient during the examination, and/or so forth.

The scan is repeated at the annual basis (or on other clinically established rate). It is advantageous to scale the obtained counts for the corresponding injected dose (that is, to scale by the radioactivity of the administered radiotracer) and to ensure that the uptake period and acquisition time are the same for each test, as well as use the same type of tracer (or employ conversion coefficient), to make the scan series directly comparable. Alternatively, if these factors cannot be made constant (for example, if the radiotracer used in a previous test becomes unavailable) then appropriate scaling of the count metric(s) may be employed based on empirical information.

Normal aging may also result in increased plaque deposition potentially leading to false positives, and this again may optionally be accounted for by scaling the count metric(s). It is also beneficial to start the testing early enough to provide a baseline of the count metric(s) during the healthy uptake period before amyloid deposits start to build up in brain tissue. It may be especially beneficial to start this tracking and do it more often for patients in certain occupations, such as professional football players, as increased beta-amyloid plaque deposition has been linked to CTE as well.

Machine learning techniques may optionally be employed to determine and empirically quantify the impact of factors and variables (e.g. age, gender, ethnicity, and so forth) that may impact the screening quantification so as to reduce the risk of false-positives. For example, any change in the body mass index (BMI) of the patient over the years, may affect the relative uptake ratio.

It is beneficial for each screening test be performed using the same camera or detector 14. If this is not possible, then a different camera may be used, but a sensitivity conversion factor between two cameras is preferably applied to ensure reproducibility and agreement in measurements.

The device 10 may use low cost radiation detection electronics with sufficient stopping power, in one example, a Bismuth Germanate Oxide (BGO) detector may be used for this purpose. No coincidence mode is necessary unless PET imaging is desired as an option, and therefore a sensitivity increase is contemplated due to singles detection mode and close positioning of the subject to the detectors 14. Further, in embodiments in which no imaging is performed, there is no requirement such as "minimum detected counts per image voxel" as it is in the case with conventional PET or SPECT systems. As attenuation in the brain remains nearly constant throughout the life of the patient, no CT acquisition or other source for an attenuation map is needed either. Rather, the impact of attenuation in the head H of the patient P is automatically accounted for by generating the amyloid metric based on comparison of the current count metric(s) with past count metric(s) from past tests performed on the same patient P.

If even 100,000 single counts are detected during the acquisition, the resulting signal noise (per a Poisson process) would only constitute less than 0.5% of the signal. This means that only microCi levels of dose injections of amyloid tracer are needed, leading to a more than 1000× dose reduction as compared to conventional PET, and making the scan comparable to dental X-ray exams in terms of radiation burden.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A device for performing an amyloid assessment, the device comprising:
   a radiation detector assembly including a plurality of radiation detectors mounted in or on a patient support; and
   at least one electronic processor programmed to:
   detect radiation counts from the plurality of radiation detectors of the radiation detector assembly over a data acquisition time interval;
   compute, from the detected radiation counts, at least one current count metric comprising a total counts detected by the plurality of radiation detectors over the data acquisition time interval, by scaling the at least one current count metric using a predetermined scaling factor based on one or more of patient weight, patient age, patient gender, and patient ethnicity;
   store the at least one current count metric associated with a current test date in a non-transitory storage medium; and
   determine an amyloid metric based on a comparison of the at least one current count metric with a count metric stored in the non-transitory storage medium associated with an earlier test date.

2. The device of claim 1 wherein the radiation detector assembly further comprises:
   a radiation shielding collar comprising a radiation-absorbing material and shaped and sized to be disposed around a neck.

3. The device of claim 1 where the plurality of radiation detectors comprises:
   a back radiation detector; and
   two side radiation detectors, wherein the back radiation detector and the two side radiation detectors are arranged to define a cavity sized to receive a head with the back radiation detector arranged to view a backside of the head disposed in the cavity and the two side radiation detectors arranged to view left and right sides of the head disposed in the cavity.

4. The device of claim 3 where the plurality of radiation detectors further comprises:
   a crown radiation detector arranged to further define the cavity with the crown radiation detector arranged to view a crown of the head disposed in the cavity.

5. The device of claim 1 wherein:
   the radiation detector assembly does not include a radiation collimator, and
   the device does not include timestamping circuitry for assigning timestamps to radiation counts detected using the radiation detector assembly; and
   the computing of the at least one current count metric from the detected radiation counts does not include performing image reconstruction on the detected radiation counts.

6. The device of claim 1 wherein:
   the radiation detector assembly includes one of (i) at least one radiation collimator or (ii) coincidence detection circuitry for acquiring the radiation counts as radiation coincidence counts; and
   the at least one electronic processor is further programmed to reconstruct the detected radiation counts into an image.

7. The device of claim 1 wherein:
the radiation detector assembly includes at least one slat radiation collimator; and
the at least one electronic processor is further programmed to reconstruct the detected radiation counts into a one-dimensional image.

8. The device of claim 7 wherein:
the radiation detector assembly does not include robotic actuators configured for moving the plurality of radiation detectors during the data acquisition time interval over which radiation counts are detected using the radiation detector assembly.

9. The device of claim 1 wherein the radiation detector assembly is configured to detect radiation counts emanating from at least one-half of a brain monitored by the radiation detector assembly.

10. A method for performing a clinical assessment, the method comprising:
obtaining imaging data using a radiation detector assembly including a plurality of radiation detectors mounted in or on a patient support on which the patient is positioned to view a head of the positioned patient;
detecting radiation counts from the plurality of radiation detectors of the radiation detector assembly based on a radiotracer administered to the patient that binds with a targeted protein over a data acquisition time interval;
computing, from the detected radiation counts, at least one current count metric comprising a total counts detected by the plurality of radiation detectors over the data acquisition time interval, by scaling the at least one current count metric using a predetermined scaling factor based on one or more of patient weight, patient age, patient gender, and patient ethnicity; and
determining a metric of deposits of the targeted protein in the head of the positioned patient based on a comparison of the at least one current count metric with a previous count metric.

11. The method of claim 10, further including:
performing a follow-up assessment of the patient using the determined metric of deposits.

12. The method of claim 10, further including:
generating a one-dimensional counts profile line from the measured total number of counts; and
controlling a display to display the generated counts profile line.

13. The method of claim 10, wherein the detecting comprises continuously detecting singles radiation counts from at least one-half of the brain of the positioned patient over the data acquisition time interval.

14. The method of claim 13, wherein the singles radiation counts are detected without collimation of the radiation.

15. The method of claim 10, wherein the targeted protein comprises beta amyloid.

\* \* \* \* \*